United States Patent [19]

Lunn

[11] 4,242,509

[45] Dec. 30, 1980

[54] PROCESS FOR PRODUCING 7-AMINO-7-ALKOXYCEPHALOSPORINS

[75] Inventor: William H. W. Lunn, Indianapolis, Ind.

[73] Assignee: Eli Lilly and Company, Indianapolis, Ind.

[21] Appl. No.: 29,792

[22] Filed: Apr. 13, 1979

Related U.S. Application Data

[60] Division of Ser. No. 853,063, Nov. 21, 1977, abandoned, which is a continuation of Ser. No. 298,165, Oct. 16, 1972, abandoned.

[51] Int. Cl.$^3$ ............................................. C07D 501/18
[52] U.S. Cl. ........................................ 544/21; 424/246
[58] Field of Search ........................................... 544/21

[56] References Cited

U.S. PATENT DOCUMENTS

| | | | |
|---|---|---|---|
| 3,780,034 | 12/1973 | Christensen et al. | 260/243 C |
| 3,897,424 | 7/1975 | Koppel et al. | 544/21 |
| 3,920,638 | 11/1975 | Bickel et al. | 260/243 C |
| 4,031,086 | 6/1977 | Karady et al. | 544/21 |
| 4,103,083 | 7/1978 | Ogawa et al. | 544/21 |

FOREIGN PATENT DOCUMENTS

| | | | |
|---|---|---|---|
| 718824 | 1/1969 | Belgium | 260/243 C |
| 10835 | 2/1969 | Netherlands | 260/243 C |
| 1239814 | 7/1971 | United Kingdom | 260/243 C |

OTHER PUBLICATIONS

C. A., vol. 71, col. 61403wc, 1969.
Karady et al., Tetrahedron Letters, No. 28, pp. 2401–2404, (1976).
Morrison et al., Organic Chemistry, pp. 741–742, (1966), 2nd Edition.

*Primary Examiner*—Nicholas S. Rizzo
*Attorney, Agent, or Firm*—Charles W. Asbrook

[57] ABSTRACT

A 7-(5-amino-5-carboxyvaleramido)-7-methoxycephalosporin with amino and acid groups protected is reacted with PCl$_5$ or other agent capable of forming an imino halide; the resulting imino halide is thereafter reacted under essentially non-aqueous conditions with a primary loweralkanol of $C_1$–$C_4$ or with methan-d$_3$-ol, yielding nucleus bearing a 7-alkoxy group derived from the primary loweralkanol or methan-d$_3$-ol. In situ acylation of the nucleus affords 7-acylamido-7-alkoxycephalosporins in good yield; these products can be deesterified to yield the corresponding acids, which exhibit antibacterial activity.

6 Claims, No Drawings

PROCESS FOR PRODUCING 7-AMINO-7-ALKOXYCEPHALOSPORINS

This is a division of application Ser. No. 853,063 filed Nov. 21, 1977, now abandoned, which is a continuation of application Ser. No. 298,165 filed Oct. 16, 1972, now abandoned.

BRIEF SUMMARY OF THE INVENTION

An article by Nagarajan et al. at *J. Am. Chem. Soc.* 93:9 (May 5, 1971) describes novel antibiotics of the following structural formulae:

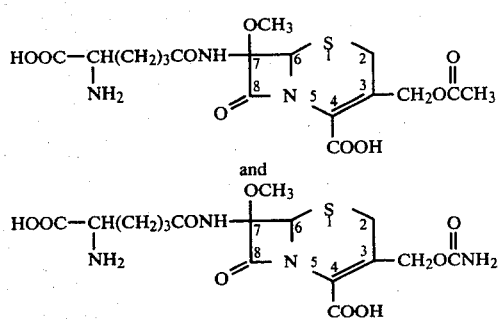

These antibiotics are named 7-(5-amino-5-carboxyvaleramido)-7-methoxycephalosporanic acid and 7-(5-amino-5-carboxyvaleramido)-7-methoxy-3-carbamoyloxymethyl-3-cephem-4-carboxylic acid, respectively. Alternatively, they are referred to as antibiotics A16884 and A16886I; cf. Belgian Pat. No. 754,424 and No. 754,693. The latter of these antibiotics is also described, as antibiotic "842A", by Belgian Patent No. 764,160.

In addition, Belgian Pat. No. 764,160 describes an antibiotic "810A" which is of the formula

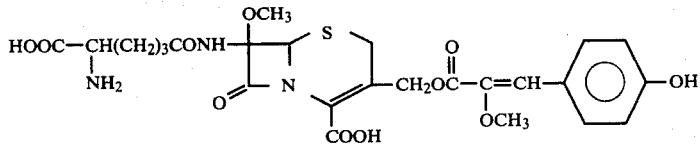

This antibiotic is named 7-(5-amino-5-carboxyvaleramido)-7-methoxy-3-(α-methoxy-p-hydroxycinnamoyloxymethyl)-3-cephem-4-carboxylic acid.

In common with other cephalosporins, these antibiotics can be treated by the $PCl_5$ method to remove the 7-acyl group and yield a nucleus, this nucleus, if desired, can be reacylated to introduce a different 7-acyl group. However, there has now been discovered an improved method for cleaving and reacylating the foregoing antibiotics, as well as other 3-position modifications thereof. In addition, the process can be used as a method of introducing into the foregoing antibiotics, or the same 3-position modifications thereof, a different 7-alkoxy moiety or a 7-methoxy-$d_3$ moiety in lieu of the original 7-methoxy group.

Thus, the present invention is in a process for preparing a compound of the formula:

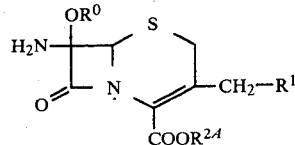

wherein $R^°$ represents primary loweralkyl of $C_1$–$C_4$ or methyl-$d_3$; $R^1$ represents acetoxy, carbamoyloxy, α-methoxy-p-hydroxycinnamoyloxy, propionyloxy, benzoyloxy, methoxy, methylthio, 1-methyl-1,2,3,4-tetrazol-5-ylthio, or 5-methyl-1,3,4-thiadiazol-2-ylthio; $R^{2A}$ represents hydrogen or $R^2$; and $R^2$ represents alkyl of $C_1$–$C_6$, 2,2,2-trichloroethyl, 2-iodoethyl, tert-alkenyl of $C_5$–$C_7$, tert-alkynyl of $C_5$–$C_7$, benzyl, ar-nitrobenzyl, tetrahydropyranyl, succinimidomethyl, phthalimidomethyl, ar-methoxybenzyl, ar,ar-dimethoxybenzyl, cyanomethyl, nitrophenyl, dinitrophenyl, 2,4,6-trinitrophenyl, bis(p-methoxyphenyl)methyl, triphenylmethyl, diphenylmethyl, benzyloxymethyl, loweralkanoyloxymethyl of $C_3$–$C_6$, or phenacyl, which process comprises reacting an imino halide compound of the formula:

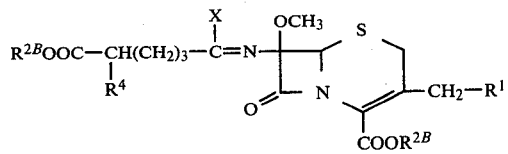

wherein $R^1$ is as defined above; $R^{2B}$ represents $R^2$ as defined above, loweralkanoyl of $C_2$–$C_4$, or radical of the formula:

wherein each $R^3$ independently represents loweralkyl of $C_1$–$C_4$ or halo selected from the group consisting of bromo, chloro, fluoro, and iodo subject to the limitation that at least one $R^3$ represents loweralkyl as defined; and $R^4$ represents an acylamido group wherein the acyl is
 alkanoyl of $C_1$–$C_4$,
 benzoyl,
 naphthoyl,
 alkoxycarbonyl of $C_2$–$C_5$,
 cycloalkoxycarbonyl of $C_6$–$C_7$,
 benzyloxycarbonyl,
 naphthyloxycarbonyl,
 one of the above groups substituted with from one to three groups, each selected from the group consisting of halo, nitro, loweralkoxy of $C_1$–$C_4$, cyano, and in the instance of benzoyl, naphthoyl, benzyloxy, and naphthyloxy, by loweralkyl of $C_1$–$C_4$, or phthaloyl;

with an alcohol of the formula R°—OH under essentially non-aqueous conditions.

The starting imino halide is preferably prepared in situ by the reaction of a compound of the formula:

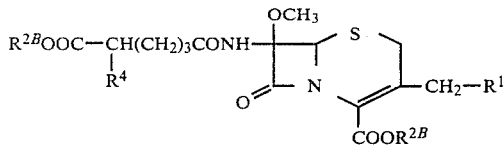

with PCl₅ or other acid halide.

Preferably, the resulting product, i.e., compound of the formula:

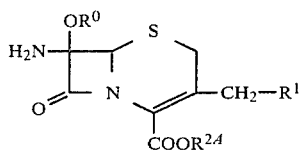

is subsequently reacylated in situ with a compound of one of the formulae

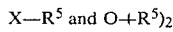

wherein X represents halogen, preferably bromine or chlorine, and
wherein
R⁵ represents
C₁-C₈ alkanoyl;
azidoacetyl;
cyanoacetyl;
haloacetyl;

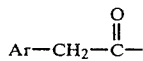

where Ar denotes phenyl, thienyl, furyl, pyrrolyl, or phenyl substituted with from one to three substituents selected from the group consisting of fluorine, chlorine, bromine, iodine, trifluoromethyl, protected amino, protected hydroxy, C₁-C₃ alkyl, C₁-C₃ alkoxy, cyano, and nitro;

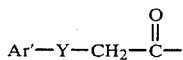

where Ar' represents phenyl, pyridyl, or substituted phenyl as defined above, and Y is oxygen or sulfur;

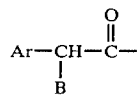

where Ar is as defined above, and B is protected amino, protected hydroxy, protected carboxy, —CN₂ or —N₃; 2-(3-sydnone) acetyl; or
2-(1H-tetrazol-1-yl)acetyl. The protected amino is preferably amino substituted by such protecting groups as benzyloxycarbonyl, p-nitrobenzyloxycarbonyl, alkoxycarbonyl of C₂-C₅, cycloalkoxycarbonyl of C₆-C₇, triphenylmethyl, or 2,2,2-trichloroethoxycarbonyl. The protected hydroxy group is preferably a group of the formula CH₃OCH₂O— or

HCO.

The protected carboxy group is preferably a carboxy group protected as described for the carboxy groups in the starting compounds.

The reacylated compounds wherein R²ᴬ represents hydrogen exhibit antibacterial activity. In the instance of compounds wherein R²ᴬ represents any of the specified ester groups, or where other protecting groups are present, the reacylated compounds can be deesterified and such other protecting groups removed to yield products exhibiting antibacterial activity.

DETAILED DESCRIPTION OF THE INVENTION

The starting materials to be employed in accordance with the present invention

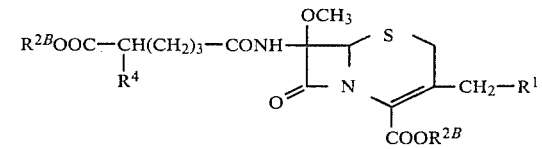

are prepared in known procedures. More particularly, antibiotic A16884, A16886I, or 810A is reacted (1) to protect the amino group, (2) to protect the acid groups, and in the case of antibiotic 810A, (3) to protect the —OH group.

The protection of the amino group is conveniently obtained by reacting antibiotic A16884, A16886I, or 810A with a suitable acyl halide, anhydride, or ketene to form an acylamido group. The identity of the acylamido group thereby formed is not critical. Suitable acylamido groups are those wherein the acyl is:
alkanoyl of C₁-C₄,
benzoyl,
naphthoyl,
alkoxycarbonyl of C₂-C₅,
cycloalkoxycarbonyl of C₆-C₇,
benzyloxycarbonyl,
naphthyloxycarbonyl,
one of the above groups substituted with from one to three groups, each selected from the group consisting of halo, nitro, loweralkoxy of C₁-C₄, cyano, and, in the instance of benzoyl, naphthoyl, benzyloxy, and naphthyloxy, by loweralkyl of C₁-C₄, or phthaloyl.

"Halo" is employed to refer to bromo, chloro, iodo, and fluoro. Representative suitable groups include the following: formyl, acetyl, propionyl, chloroacetyl, dichloroacetyl, benzoyl, p-nitrobenzoyl, phthaloyl, p-methoxybenzoyl, cyclohexyloxycarbonyl, tert-butoxycarbonyl, phenoxycarbonyl, benzyloxycarbonyl, and the like. For convenience in separating the protected amino compound, a salt thereof can be prepared.

In one embodiment, the carboxyl groups are protected by esterification. The identity of the ester group is not critical; suitable groups are those which can easily be split off after the protection is no longer required. Representative and suitable groups, when the esterification is carried out as a separate step, include alkyl of $C_1$-$C_6$, 2,2,2-trichloroethyl, 2-iodoethyl, tert-alkenyl of $C_5$-$C_7$, tert-alkynyl of $C_5$-$C_7$, benzyl, ar-nitrobenzyl, tetrahydropyranyl, succinimidomethyl, phthalimidomethyl, ar-methoxybenzyl, ar,ar-dimethoxybenzyl, cyanomethyl, nitrophenyl, dinitrophenyl, 2,4,6-trinitrophenyl, bis(p-methoxyphenyl)methyl, triphenylmethyl, diphenylmethyl, benzyloxymethyl, loweralkanoyloxymethyl of $C_3$-$C_6$, and phenacyl.

In a second and often preferred embodiment, the protection of the carboxyl groups is carried out as an initial part of the cleavage reactions, by employing either a reactant which will form a mixed anhydride, or a silane compound. The mixed anhydride is prepared in conventional procedures, as, for example, by reacting the antibiotic with an acyl halide. The identity of the latter reactant, and its corresponding moiety in the mixed anhydride, is not critical. Suitable groups include the loweralkanoyl moieties and such moieties bearing substituents. However, owing to their ease of preparation, the simple loweralkanoyl groups, such as those containing from 2 to 4 carbon atoms, are preferred.

The silane compound to be used in protection of the carboxyl groups is suitably a compound of the formula

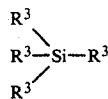

wherein each $R^3$ independently represents loweralkyl of $C_1$-$C_4$ or halo selected from the group consisting of bromo, chloro, fluoro, and iodo—subject to the limitation that at least one $R^3$ represents halo and at least one $R^3$ represents loweralkyl as defined. A preferred silane compound is trimethylchlorosilane. Other suitable compounds include dimethyldichlorosilane, methyltrichlorosilane, diethyldifluorosilane, bromotrimethylsilane, and the like. The

protecting group can also be introduced by reacting the antibiotic with a silylamide, urea, urethane, or like compound, as described in Belgian Pat. No. 737,761.

In the case of both the silyl ester and mixed anhydride protecting groups, the reaction of the imino halide with alcohol in accordance with the present invention removes such groups, yielding nucleus as free acid.

Alternately, the carboxyl and amino groups in the α-amino-adipoyl side chain can be blocked by ring formation as, for example, by formation of an imidazolidine ring.

In the case of antibiotic 810A, protection of the —OH group is readily achieved by known procedures, e.g., by reaction with chloromethyl methyl ether or with p-bromophenacyl bromide (see Fieser & Fieser, Reagents for Organic Synthesis, John Wiley & Sons, New York 1968, Vol. I, page 133 and Vol. III, page 34, respectively).

Those compounds to be employed as starting materials wherein $R^1$ represents propionyloxy, benzoyloxy, methoxy, methylthio, 1-methyl-1,2,3,4-tetrazol-5-ylthio, or 5-methyl-1,3,4-thiadiazol-2-ylthio are prepared as described in Belgian Pat. No. 768,528. The compounds can then be treated, as described above, to protect the amino and acid groups.

By whichever procedures obtained, the resulting protected compound:

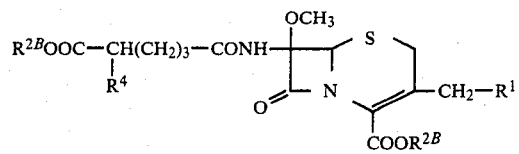

is thereafter reacted with an agent capable of forming an imino halide. While phosphorus pentachloride is the preferred agent, other acid halides can be used. Thus, other suitable agents include phosphorus oxychloride, phosphorus trichloride, thionyl chloride, phosgene, oxalyl chloride, and the complex compound formed from o-dihydroxybenzene and phosphorus trichloride.

The starting compound and the imino-halide-forming agent are reacted with one another in any convenient fashion. Generally, good results are obtained when employing the reactants in amounts representing one molecular proportion of the starting compound and from two to five molecular proportions of the imino-halide-forming agent. The reaction goes forward under temperatures of from −50° to 50° C., but is preferably conducted at about room temperatures. The reaction goes is preferably conducted in the presence of a tertiary amine, for example, triethylamine, pyridine, or dimethylaniline.

This reaction produces an imino halide of the formula:

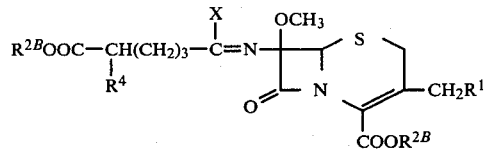

which is thereafter reacted, without separation, in the critical step of the present invention.

It has been found that when the imino halide is treated with an alcohol as defined in the present invention, there is obtained, directly, the desired nucleus:

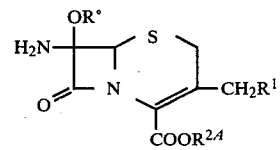

Use of an alcohol in accordance with the present invention obviates the need for water, as described by the prior art, and thereby obviates risk of degradation of the nucleus, which appears to be of lesser stability under aqueous conditions.

In addition to the foregoing advantages, use of an alcohol as herein defined provides a method for introducing a different 7-alkoxy group or for introducing the methoxy-$d_3$ group. The precise mechanism is not understood, but treatment with an alcohol in accordance with the present invention results in a nucleus bearing a 7-alkoxy group derived from the alkanol employed.

When it is desired to retain a 7-methoxy group, methanol is to be used.

The introduction of the 7-alkoxy group from the alcohol is accompanied by some epimerization at the 7-position. Antibiotics A16884, A168861, and 810A (as well as the other 3-position derivatives thereof) are believed to exist in the 7-α-methoxy configuration, the 7-(5-amino-5-carboxyvaleramido) group being in the β-configuration. Reacylated compounds prepared in accordance with the present invention exist as a mixture of α- and β-alkoxy compounds; the precise ratio varies with the particular acyl moiety.

The alcohol to be used in this step of the present process can be any primary loweralkanol of $C_1$–$C_4$, i.e., methanol, ethanol, n-propanol, n-butanol, or isobutanol; or the alcohol can be methan-$d_3$-ol. In carrying out the reaction, the alcohol is added to a solution containing the imino halide intermediate. It is essential for good yields that the solution be essentially non-aqueous and that it be maintained essentially non-aqueous until the nucleus has been reacylated. The reaction goes forward over a range of temperatures, such as from −70° to +50° C.; however, the reaction is preferably conducted initially at 0° C., followed by warming to room temperatures for a few minutes, then returning to 0° C.

The proportions of imino halide and alcohol are not critical and vary with the precise reaction and reactants. It is believed that the reaction of imino halide and alcohol, per se, consumes two molecular proportions of the alcohol per molecular proportion of the imino halide. However, additional alcohol is consumed by excess $PCl_5$ or other acid halide. Also, where the acid groups are protected by a mixed anhydride or silyl group ($R^2$=loweralkanoyl or

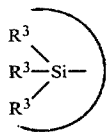

alkanol is consumed by reaction with these groups. In practice, it has been found that good results are obtained by employing the alcohol is large excess, such as five to ten molecular proportions of alcohol per molecular proportion of imino halide.

The product:

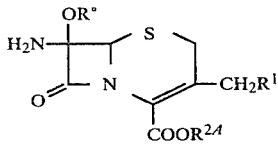

can be separated from the reaction mixture, if desired; however, such separation should be carried out under slightly basic conditions. Better results are obtained when the product is reacylated in situ. The reacylation is accomplished by reaction with a compound of one of the formulae X—$R^5$ and O—$R^5)_2$ wherein X and $R^5$ are as defined hereinabove. The acylation reaction is conducted in accordance with conventional procedures. The resulting compounds:

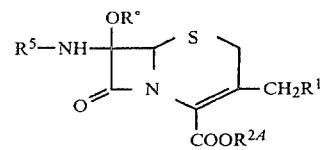

are useful, in that those of the compounds wherein $R^{24}$= an ester group can be hydrolyzed to the free acid compounds ($R^{24}$=H). The free acids with the OR° group in α configuration are useful as antibacterial agents; see Belgian Pat. No. 768,528. In the β—OR° epimer form, the esters can be treated in accordance with the process of the present invention, to yield a mixture of α- and β-alkoxy esters, the α-alkoxy epimers being useful as described above.

The following examples illustrate the practice of the present invention and will enable those skilled in the art to practice the invention. In numerous of the syntheses reported in these examples, deuterated compounds were utilized as solvents and as reagents other than the reactant, to enable easy identification of product by nmr spectroscopy. The use of such deuterated compounds is therefore not critical to the practice of the invention.

EXAMPLE 1

Preparation of 7-amino-7-methoxycephalosporanic acid, methyl ester 7-(5-Phthalimido-5-carboxyvaleramido)-7-methoxycephalosporanic acid, dimethyl ester (60.4 milligrams; 0.1 millimole) was mixed at room temperature with methylene chloride-$d_2$ (0.5 milliliter), pyridine-$d_5$ (21 milligrams; 0.25 millimole), and phosphorus pentachloride (42 milligrams; 0.2 millimole). The reaction mixture was maintained for about one hour, then cooled to 0° C. and maintained thereat for about another hour. Methanol-d (50 milligrams; 1.44 millimoles) was added and the reaction mixture held for one-half hour, yielding the desired 7-amino-7-methoxycephalosporanic acid, methyl ester in situ.

In a representative such preparation, the reaction mixture was monitored by nmr spectroscopy. The addition of the phosphorus pentachloride resulted in a downfield shift of the signal for the α-methylene group of the valeramido side chain. Prior to addition of the phosphorus pentachloride, there was a broad 4-proton resonance centered about 2.35 ppm; after the addition (but prior to addition of methanol), there was a 2-proton triplet at 2.74 ppm (J~7 cps), indicating formation of the imino chloride. Following addition of the methanol, the triplet disappeared and a 4-proton resonance, centered at 2.35 ppm, was reestablished.

EXAMPLE 2

Preparation of 7-phenoxyacetamido-7-methoxycephalosporanic acid, methyl ester

To the reaction mixture containing 7-amino-7-methoxycephalosporanic acid, methyl ester (prepared as described Example 1), chloroform-d (0.5 milliliter), pyridine-$d_5$ (127 milligrams; 1.52 millimoles), and phenoxyacetyl chloride (131 milligrams; 0.77 millimole) were added at 0° C. The reaction mixture was maintained at 0° C. for 15 minutes and then warmed up to room temperature for 10 minutes. The reaction mixture was then worked up in conventional procedures; these procedures were essentially the same as those reported hereinbelow in Example 9 beginning with the addition of dry methanol, except that methylene chloride was used, herein, in lieu of the chloroform reported in Example 9. The resulting methylene chloride phase was chromatographed on thick layer plates with benzene/ether 7:3 as developer and acetone as eluent. Mass spectra showed a parent peak at 150, consistent with the calculated molecular formula (450.4) for the expected 7-phenoxyacetamido-7-methoxycephalosporanic acid, methyl ester. The compound was also subjected to high resolution mass spectroscopy; it indicated a parent ion with mass 450.1106 (theory for $C_{20}H_{22}N_2O_8$ S, 450.1097).

In a representative preparation as described above, the product was subjected to nmr spectroscopy in $CDCl_3 = \delta 2.05$ (s, 3H, 3—$CH_2OCOC\underline{H}_3$); 3.41 (two q, 2H, 2—$C\underline{H}_2$); 3.51 and 3.54 (two s, 3H, 7—$OC\underline{H}_3$ two epimers); 3.87 (s, 3$\underline{H}$, 4—$COOC\underline{H}_3$); 4.08 (broad, 2H, $\phi OC\underline{H}_2CONH$); 4.96 (two q, 2H, 3—$CH_2OCOC\underline{H}_3$); 5.12 (s, ~0.15H, 6—$\underline{H}$ of 7-α—$OCH_3$ epimer); and 5.23 ppm (s, ~0.85H, 6$\underline{H}$ of 7-β—$OCH_3$ epimer).

EXAMPLE 3

Preparation of 7-amino-7-methoxycephalosporanic acid 8-(5-Phthalimido-5-carboxyvaleramido)-7-methoxycephalosporanic acid (57.6 milligrams; 0.1 millimole) was mixed with 0.5 milliliter of methylene chloride-d$_2$ and the mixture cooled to 0° C. Dimethylaniline (80.5 milligrams; 0.72 millimole) and acetyl chloride-d$_3$ (28.5 milligrams; 0.35 millimole) were added and the reaction mixture maintained at 0° C. and vibrated. Within fifteen minutes, all substances had gone into solution; an hour later, phosphorus pentachloride (73 milligrams; 0.35 millimole) was added and the reaction mixture likewise vibrated. Within 25 minutes the phosphorus pentachloride had gone into solution, and the reaction mixture was held for several hours. The reaction mixture was then stored in dry ice for two hours and subsequently brought up to 0° C. Methanol-d (96 milligrams; 3.0 millimole) was added and the reaction mixture vibrated and brought up to room temperature five minutes later, yielding in situ the desired 7-amino-7-methoxycephalosporanic acid.

EXAMPLE 4

Preparation of 7-phenoxyacetamido-7-methoxycephalosporanic acid

To the final reaction mixture reported in Example 3, chloroform-d (0.5 milliliter), pyridine-d$_5$ (276 milligrams; 3.5 millimoles), and phenoxyacetyl chloride (273 milligrams; 1.6 millimoles) were added at 0° C. and the resulting reaction mixture vibrated. Twenty minutes later, 0.5 milliliter of chloroform and 96 milligrams of methanol (3.0 millimoles) were added. The reaction mixture was diluted to 10 milliliters with chloroform, extracted with two 15-milliliter portions of sodium bicarbonate solution, and the sodium bicarbonate solutions washed with 20 milliliters of chloroform. The chloroform and sodium bicarbonate layers were separated and 50 milliliters of chloroform were added to the sodium bicarbonate layer, and it was then acidified to pH 2.5 with phosphoric acid and the chloroform layer separated. The solution was extracted again with 20 milliliters of chloroform. The last two chloroform layers, obtained from the acidified bicarbonate solution were combined and evaporated, yielding a total of 35.2 milligrams of 7-phenoxyacetamido-7-methoxycephalosporanic acid.

EXAMPLE 5

Preparation of 7-phenoxyphenacetamido-7-methoxycephalosporanic acid,

7-Phenoxyacetamido-7-methoxycephalosporanic acid was prepared in the same procedures as reported in Examples 3–4, except that 7-(5-chloroacetamido-5-carboxyvaleramido)-7-methoxycephalosporanic acid (52.2 milligrams; 0.1 millimole) was employed as the starting material. Other reactants and materials were, initially, methylene chloride-d$_2$ (0.5 milliliter); N,N-dimethylaniline (80.5 milligrams; 0.72 millimole); and acetyl chloride-d$_3$ (28.5 milligrams; 0.35 millimole); then phosphorus pentachloride (73 milligrams; 0.35 millimole); subsequent reagents and amounts, and the workup procedures, were the same as in Examples 3 and 4. Workup yielded 454 milligrams of 7-phenoxyacetamido-7-methoxycephalosporanic acid.

EXAMPLE 6

Preparation of 7-amino-7-methoxy-d$_3$-cephalosporanic acid, methyl ester

7(5-Phthalimido-5-carboxyvaleramido)-7-methoxycephalosporanic acid, dimethyl ester (60.4 milligrams; 0.1 millimole), methylene chloride-d$_2$ (0.5 milliliter), and pyridine-d$_5$ (21 milligrams; 0.31 millimole) were mixed at room temperature and phosphorus pentachloride (42 milligrams; 0.2 millimole) added. The reaction mixture was held for about five hours. The reaction mixture was then cooled to 0° C. and methan-d$_3$-ol-d (52 milligrams; 1.44 millimoles) added. As a result of these operations, there was obtained in situ the desired 7-amino-7-methoxy-d$_3$-cephalosporanic acid, methyl ester.

EXAMPLE 7

Preparation of 7-phenoxyacetamido-7-methoxy-d$_3$-cephalosporanic acid, methyl ester To the reaction mixture obtained as reported in Example 6, there was added chloroform-d (0.5 milliliter), pyridine-d$_5$ (127 milligrams; 1.52 millimole), and phenoxyacetyl chloride (131 milligrams; 0.77 millimole). The reaction mixture was thereafter treated as described in Example 9. After conventional workup, there was obtained 18 milligrams of the starting 7-(5-phthalimido-5-carboxyvaleramido)-7-methoxycephalosporanic acid, dimethyl ester; 16.2 milligrams of 7-(5-phthalimido-5-carbomethoxy-d$_3$-valeramido)-7-methoxycephalosporanic acid, methyl ester; 111 milligrams of phenoxyacetic acid, methyl-d$_3$ ester; and 19 milligrams of the desired 7-phenoxyacetamido-7-methoxy-d$_3$-cephalosporanic acid, methyl ester. High resolution mass spectroscopy of the 7-phenoxyacetamido-7-methoxy-d$_3$-cephalosporanic acid, methyl ester, showed a parent peak with mass 453.1277 (theory for $C_{20}D_3H_{19}N_2O_8S$, 453.1285). Nmr spectroscopy (CDCl$_3$) showed $\delta$2.09 (s,3H,3-CH$_2$OCOC$\underline{H}_3$); 3.45 (m,2H,2—C$\underline{H}_2$); 3.91 (t,3H, 4—COOC$\underline{H}_3$); 4.61 and 4.62 (2 sharp peaks, total 2H, $\phi$OC$\underline{H}_2$CONH); 4.98 (q,2H,3—C$\underline{H}_2$-OCOCH$_3$); and 5.15 and 5.26 ppm (2 sharp peaks, 0.3H and 0.7H, respectively, 6-$\underline{H}$ of 7-α—OCH$_3$ and 7-β—OCH$_3$ epimers, respectively).

EXAMPLE 8

Preparation of 7-amino-7-methoxycephalosporanic acid, benzhydryl ester 7-(5-Phthalimido-5-carboxyvaleramido)-7-methoxycephalosporanic acid, dibenzhydryl ester (910 milligrams; 1 millimole) was dissolved in 5 milliliters of methylene chloride and the solution stirred at 0° C. Pyridine (0.198 gram; 0.20 milliliter; 2.5 millimoles) was then added, followed by phosphorus pentachloride (0.42 gram; 2.0 millimoles). The reaction mixture was stirred at room temperature for 1.5 hours. Anhydrous methanol (0.46 gram; 0.59 milliliter; 14.4 millimole) was then added, followed by 10 minutes stirring at 0° C. and 5 minutes stirring at room temperature. The resulting reaction mixture, containing the desired 7-amino-7-methoxycephalosporanic acid, benzhydryl ester, was again cooled to 0° C. and divided into two portions.

EXAMPLE 9

Preparation of 7-phenoxyacetamido-7-methoxycephalosporanic acid, benzhydryl ester To one of the portions of reaction mixture prepared as described in Example 8 and containing 7-amino-7-methoxycephalosporanic acid, benzhydryl ester, there was added chloroform (2.5 milliliters) containing pyridine (0.60; 7.6 millimoles). The reaction mixture was stirred for 5 minutes, then phenoxyacetyl chloride (0.68 gram; 3.85 millimoles) was added. The reaction mixture was stirred at 0° C. for 15 minutes, then at room temperature for 10 minutes. Dry methanol (0.3 milliliter) was added and the reaction mixture stirred at room temperature for another 5 minutes. The reaction mixture was subsequently poured into ice water and the chloroform phase washed with dilute HCl, then with several volumes of water, and then dried sequentially over sodium chloride and over magnesium sulfate. The chloroform was removed on a rotary evaporator, yielding an oil, 1.14 gram.

This oil was chromatographed and the fraction containing 7-phenoxyacetamido-7-methoxycephalosporanic acid, benzhydryl ester, separated and subjected to nmr spectroscopy (CDCl$_3$): δ 1.97, 1.98 (two s, 3H, 3—CH$_2$OCOC$\underline{H}_3$); 3.4 (two q, 2H, 2—C$\underline{H}_2$); 3.54 (broad, 3H, 7—OC$\underline{H}_3$); 4.56 (two s, 2H, φOC$\underline{H}_2$-CONH); 4.9 (two q, 2H, 3—C$\underline{H}_2$OCOCH$_3$); 5.11 (s, 0.4H, 6—$\underline{H}$ of 7-α—OCH$_3$ epimer); and 5.24 ppm (s, 0.6H, 6—$\underline{H}$ of 7-β-OCH$_3$ epimer).

The same fraction was chromatographed into two portions, one containing the 7-β-methoxy stereoisomer (32 milligrams), the other containing both 7-α-methoxy and 7-β-methoxy epimers (57 milligrams).

EXAMPLE 10

Preparation of 7-β-phenoxyacetamido-7-α-methoxy-cephalosporanic acid

The fraction prepared as described in Example 9 and containing both 7-α-methoxy and 7-β-methoxy epimers was thereafter treated to remove the benzhydryl ester. The fraction was dissolved in a 1:1 mixture of trifluoroacetic acid-formic acid (0.2 milliliter) and after 5 minutes at room temperature, methylene chloride (4-milliliters) was added and the mixture rotary evaporated to dryness at room temperature. Ethyl acetate was added and the mixture extracted with dilute sodium bicarbonate. The sodium bicarbonate extract was washed with ethyl acetate, then acidified to pH 1.5 under ethyl acetate. The phases were then separated and the ethyl acetate extract dried over magnesium sulfate, filtered, and evaporated to dryness.

The foregoing procedures yielded and α-epimer, 7-β-phenoxyacetamido-7-α-methoxycephalosporanic acid: nmr (CDCl$_3$), δ 2.06 (s, 3H, 3—CH$_2$OCOC$\underline{H}_3$); 3.36 (q, 2H, 2—C$\underline{H}_2$; 3.54 (s, 3H, 7—OC$\underline{H}_3$); 4.61 (broad, 2H, φOC$\underline{H}_2$CONH); 5.04 (q, 2H, 3—C$\underline{H}_2$-OCOCH$_3$); and 5.12 ppm (s, 1H, 6—H).

EXAMPLE 11

PREPARATION OF 7-ACETAMIDO-7-METHOXYCEPHALOSPORANIC ACID, BENZHYDRYL ESTER

The second portion of reaction mixture prepared as described in Example 8 and containing 7-amino-7-methoxycephalosporanic acid, benzhydryl ester, was acylated with acetyl chloride. The procedures and reagents other than the acyl halide were the same as those reported in Example 9. As a result, there was obtained 7-acetamido-7-methoxycephalosporanic acid, benzhydryl ester: nmr (CDCl$_3$) δ1.96 and 1.97 (two s, 6H, 3—CH$_2$OCOC$\underline{H}_3$ and 7—C$\underline{H}_3$CONH); 3.38 (q, 2H, 2—C$\underline{H}_2$); 3.50 (broad, 3H, 7—OC$\underline{H}_3$); 4.81 (two q, 2H, 3—C$\underline{H}_2$OCOCH$_3$); 5.10 (s projecting from another signal, 6—$\underline{H}$ of 7-α—OCH$_3$ epimer); and 5.20 ppm (s, 0.6H, 6—$\underline{H}$ of 7-β-OCH$_3$ epimer).

I claim:

1. The process for preparing a compound of the formula:

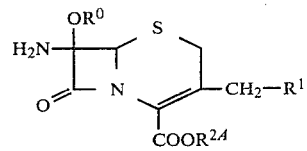

wherein R° represents primary loweralkyl of C$_1$-C$_4$ or methyl-d$_3$; R$^1$ represents acetoxy, carbamoyloxy, α-methoxy-p-hydroxycinnamoyloxy, propionyloxy, benzoyloxy, methoxy, methylthio, 1-methyl-1,2,3,4-tetrazol-5-ylthio, or 5-methyl-1,3,4-thiadiazol-2-ylthio; R$^{2A}$ represents hydrogen or R$^2$; and R$^2$ represents alkyl of C$_1$-C$_6$, 2,2,2-trichloroethyl, 2-iodoethyl, tert-alkenyl of C$_5$-C$_7$, tert-alkynyl of C$_5$-C$_7$, benzyl, ar-nitrobenzyl, tetrahydropyranyl, succinimidomethyl, phthalimidomethyl, ar-methoxybenzyl, ar, ar-dimethoxybenzyl, cyanomethyl, nitrophenyl, dinitrophenyl, 2,4,6-trinitrophenyl, bis(p-methoxyphenyl)methyl, triphenylmethyl, diphenylmethyl, benzyloxymethyl, loweralkanoyloxymethyl of C$_3$-C$_6$, or phenacyl; which process comprises reacting an imino halide compound of the formula:

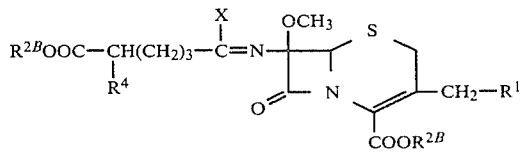

wherein X represents bromide or chloride; R$^1$ is as defined above; R$^{2B}$ represents R$^2$ as defined above, loweralkanoyl of C$_2$-C$_4$ or radical of the formula:

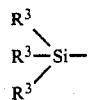

wherein each $R^3$ independently represents loweralkyl of $C_1$-$C_4$ or halo selected from the group consisting of bromo, chloro, fluoro, and iodo subject to the limitation that at least one $R^3$ represents loweralkyl as defined; and $R^4$ represents an acylamido group wherein the acyl is
- alkanoyl of $C_1$-$C_4$,
- benzoyl,
- naphthoyl,
- alkoxycarbonyl of $C_2$-$C_5$,
- cycloalkoxycarbonyl of $C_6$-$C_7$,
- benzyloxycarbonyl,
- naphthyloxycarbonyl,
- one of the above groups substituted with from one to three groups, each selected from the group consisting of halo, nitro, loweralkoxy of $C_1$-$C_4$, cyano, and in the instance of benzoyl, naphthoyl, benzyloxy, and naphthyloxy, by loweralkyl of $C_1$-$C_4$, or
- phthaloyl;

with an alcohol of the formula $R^\circ$—OH under essentially non-aqueous conditions.

2. The process of claim 1 wherein $R^1$ is acetoxy.

3. The process of claim 1 wherein $R^1$ is carbamoyloxy.

4. The process of claim 1 wherein the product is subsequently reacted in situ with a compound of one of the formula:

wherein X represents bromo or chloro and $R^5$ represents
- $C_1$-$C_8$ alkanoyl;
- azidoacetyl;
- cyanoacetyl;
- haloacetyl;

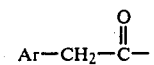

where Ar denotes phenyl, thienyl, furyl, pyrrolyl, or phenyl substituted with from one to three substituents selected from the group consisting of fluorine, chlorine, bromine, iodine, trifluoromethyl, hydroxy, $C_1$-$C_3$ alkyl, $C_1$-$C_3$ alkoxy, cyano, and nitro;

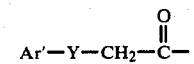

where Ar' represents phenyl, pyridyl, or substituted phenyl as defined above, and Y is oxygen or sulfur;

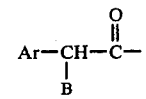

where Ar is as defined above, and B is protected amino, protected hydroxy, protected carboxy, —CN, or —$N_3$;
- 2-(3-sydnone)acetyl; or
- 2-(1H-tetrazol-1-yl)acetyl.

5. The process of claim 4 wherein $R^1$ represents acetoxy.

6. The process of claim 4 wherein $R^1$ represents carbamoyloxy.